United States Patent

Shroot et al.

Patent Number: 4,548,942
Date of Patent: Oct. 22, 1985

[54] ANTI-ACNE USE OF DERIVATIVES OF (5,4B)-ISOTHIAZOLO PYRIDINE-3-ONE

[75] Inventors: Braham Shroot, Antibes; Jean Maignan, Tremblay les Gonesse, both of France

[73] Assignees: Societe Anonyme dite: L'Oreal; Groupement d'Interet Economique dit: Centre International de Recherches Dermatologiques C.I.R.D., both of Paris, France

[21] Appl. No.: 554,699

[22] Filed: Nov. 23, 1983

[30] Foreign Application Priority Data

Nov. 26, 1982 [LU] Luxembourg ............ 84491

[51] Int. Cl.⁴ .................................. A61K 31/435
[52] U.S. Cl. .................................. 514/301; 514/859
[58] Field of Search ............ 424/256; 546/114

[56] References Cited

U.S. PATENT DOCUMENTS 3,965,107 6/1976 Rainey et al. .............. 546/114

FOREIGN PATENT DOCUMENTS 2349591 11/1977 France .

OTHER PUBLICATIONS

Journal of Heterocyclic Chemistry, Nov.-Dec. 1982, vol. 19, No. 6, pp. 1393-1396.
Die Pharmazie, Sep. 1974, pp. 561, 597-602.
Chemical Abstracts, 88:50843q, 1978, (Baggaley).

Primary Examiner—Leonard Schenkman
Attorney, Agent, or Firm—Cushman, Darby & Cushman

[57] ABSTRACT

An anti-acne composition comprises in a carrier suitable for topical application to the skin an active compound having the formula

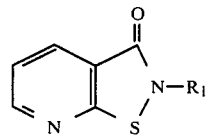

wherein $R_1$ is linear or branched alkyl having 1–12 carbon atoms, mono- or polyhydroxyalkyl having 2–5 carbon atoms, alkenyl having 3–6 carbon atoms, cycloalkyl having 3–6 carbon atoms, or a radical of the formula

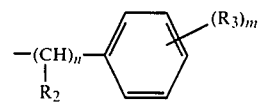

wherein n is 0 or 1, m is 1, 2 or 3, $R_2$ is hydrogen or lower alkyl having 1–3 carbon atoms and $R_3$ represents hydrogen, alkyl having 1–4 carbon atoms, nitro, —$CF_3$ or halogen. The acid salts of these active compounds can also be used.

9 Claims, No Drawings

ANTI-ACNE USE OF DERIVATIVES OF (5,4B)-ISOTHIAZOLO PYRIDINE-3-ONE

The present invention relates to a new anti-acne composition containing, as an active component, a derivative of (5,4b)-isothiazolo pyridine-3-one.

Acne is generally manifested by the appearance of pimples, blackheads or pustules on the face, the neck and at times on the back and chest. This manifestation of acne is caused, essentially, by the hyperkeratinization of the ducts of the sebaceous glands. As a result the sebum which is not able to flow freely, forms a favorable environment for bacterial proliferation. This leads to certain inflammation phenomena, the bacteria being in effect capable of rupturing the ducts of the sebaceous glands which free irritating fatty acids.

In an effort to avoid such irritating phenomena, it is important to employ certain substances capable of acting, in an efficacious manner, with regard to the principal germs associated with acne, i.e. *Corinebacterium acnes* and *Propionibacterium granulosum*.

When the activity of these germs are inhibited the hydrolytic cleavage of normal triglycerides of sebum is avoided thereby preventing the formation of long chain fatty acids, the presence of which, as has been noted, causes typical inflammation phenomena of acne lesions.

The active compounds of the compositions according to the present invention are, in this respect, excellent anti-acne agents especially since they have been established as being particularly selective with regard to the two principal germs associated with acne, i.e. *Corinebacterium acnes* and *Propionibacterium granulosum*.

Tests carried out using these active components by the tablet diffusion method verified and confirmed this specificity for these two germs.

The present invention thus relates to, as a new industrial product, an anti-acne composition comprising in a carrier suitable for topical application to the skin at least one active compound having the following formula:

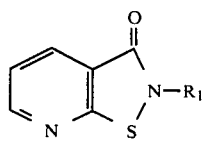
(I)

wherein $R_1$ is a linear or branched alkyl having 1–12 carbon atoms, a mono- or polyhydroxyalkyl having 2 to 5 carbon atoms, alkenyl having 3 to 6 carbon atoms, cycloalkyl having 3 to 6 carbon atoms or a radical of the formula

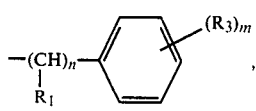
(II)

wherein n is 0 or 1, m is 1, 2 or 3, $R_2$ represents hydrogen or lower alkyl having 1–3 carbon atoms and $R_3$ represents hydrogen, alkyl having 1–4 carbon atoms, nitro, —$CF_3$ or a halogen, and their salts of a mineral or organic acid, such as hydrochloric acid or hydrobromic acid.

The linear or branched alkyl having 1–12 carbon atoms is preferably methyl, ethyl, propyl isopropyl, butyl, octyl or nonyl.

The cycloalkyl radical is preferably cyclopentyl or cyclohexyl.

The radical of formula II is preferably phenyl, benzyl, p-tolyl, 2′,5′-dichlorophenyl, 2′,4′-dichlorophenyl, 4′-chlorophenyl, 4′-nitrophenyl, 4′-methylbenzyl, 4′-nitrobenzyl, 4′-chlorobenzyl, 2′,4′-dichlorobenzyl and 2′,5′-dichlorobenzyl.

According to a preferred embodiment the composition according to the present invention contains a compound of formula (I) wherein the radical $R_1$ represents a mono- or polyhydroxyalkyl having 2–5 carbon atoms, alkenyl having 3–6 carbon atoms or cycloalkyl having 3–6 carbon atoms.

Representative preferred active compounds of formula (I) for use in the compositions according to the present invention include:

(1) 2-methyl-(5,4b)isothiazolo pyridine-3-one,
(2) 2-ethyl-(5,4b)isothiazolo pyridine-3-one,
(3) 2-isopropyl-(5,4b)isothiazolo pyridine-3-one,
(4) 2-octyl-(5,4b)isothiazolo pyridine-3-one,
(5) 2-(2-hydroxypropyl)-(5,4b)isothiazolo pyridine-3-one,
(6) 2-(1,2-dihydroxypropyl)-(5,4b)-isothiazolo pyridine-3-one,
(7) 2-cyclohexyl-(5,4b)-isothiazolo pyridine-3-one,
(8) 2-benzyl-(5,4b)-isothiazolo pyridine-3-one,
(9) 2-(p-chlorophenyl)-(5,4b)-isothiazolo pyridine-3-one, and
(10) 2-(2,5-dichlorophenyl)-(5,4b)-isothiazolo pyridine-3-one.

In the compositions according to the present invention the concentration of the active compounds of formula (I) is generally between 0.05 and 10 percent, and preferably between 0.3 and 3 percent, by weight based on the total weight of the composition.

These compositions can be provided under various forms appropriate for topical application on the area of the skin to be treated and principally under the form of a lotion, an ointment, a powder, a milk, a cream, a gel or under the form of an aerosol.

The lotions are aqueous or hydroalcoholic liquid preparations capable of also containing certain suspension or dispersion agents such as cellulose derivatives, gelatine and gums as well as glycerine or propylene glycol.

The gels are semi-solid preparations prepared by gelling a solution or suspension of an active compound of formula (I) using a gelling agent such as "bentone gel" (sold by N.L. Industrie) for a fatty phase or cross-linked polyacrylic acid, for an aqueous phase, this polyacrylic acid being sold by Goodrich under the tradename "Carbopol", and being employed in the neutralized form.

According to a preferred embodiment, the compositions according to the present invention are provided in the form of a cream, that is to say, in the form of a water-in-oil or oil-in-water emulsion.

Representative oils usefully employed as the oil phase in these emulsions include, for instance:

animal oils such as horse oil, hog oil and lanolin; vegetable oils such as sweet almond oil, avoacado oil, ricin oil, olive oil, grape seed oil, poppy seed oil, colza oil, peanut oil, corn oil, hazelnut oil, jojoba oil, safflower oil, and wheat germ oil;

hydrocarbon oils such as paraffin oil, Purcellin oil, perhydrosqualene and solutions of microcrystalline wax in oils;

mineral oils and principally oils having an initial distillation point at atmospheric pressure of about 250° C. and a final distillation point on the order of 410° C.; and silicone oils soluble in other oils.

Certain synthetic products such as, for example, saturated esters and principally, isopropyl palmitate, isopropyl myristate, butyl myristate, cetyl myristate, hexadecyl stearate, ethyl palmitate as well as the triglycerides of octanoic or decanoic acids and cetyl ricinoleate can also be employed in the anti-acne compositions of the present invention.

The oil phase of these emulsions can also contain certain waxes and principally carnauba wax, beeswax, ozokerite or candellila wax.

These emulsions can also contain known emulsifying agents or mixtures of such agents, such as those having a total average HLB between 1 and 14, and particularly between 3 and 13, for example, a mixture of triethanolamine stearate and oxyethylenated stearic acid, oleic alcohol oxyethylenated with 10 moles of ethylene oxide and glycerol monostearate.

In these emulsions, the emulsifying agent is generally present in an amount between 1 and 12 percent relative to the total weight of the composition.

The compositions of the present invention in the form of a cream can also contain other components such as preservatives, perfumes, dyes, sunscreen agents, pigments, humectants, charges such as talc, nylon powder, starch powder, polyethylene powder and the like.

In order to reinforce the anti-acne activity of the active compounds of formula (I) it is possible to employ, in accordance with the invention, certain antibiotics such as tetracyclines such as, for example, chlorotetracycline or oxytetracycline, or macrolids such as erythromycin, aminosides such as neomycin, sulfamides (sulfanilamides), synergistines, A.B. polypeptides or chloramphenicol.

The treatment of acne using the compositions according to the present invention comprises applying a sufficient amount of the composition, two or three times each day, to the area of the skin to be treated and this for a period of time ranging from one to six weeks.

Certain ones of the active compounds of formula (I) are known compounds. These known compounds are those wherein $R_1$ represents linear or branched alkyl having 1–12 carbon atoms or a radical of formula (II).

However, compounds wherein $R_1$ represents a mono- or polyhydroxyalkyl having 2–5 carbon atoms or alkenyl having 3–6 carbon atoms or cycloalkyl having 3–6 carbon atoms, are new. These compounds can be obtained in accordance with the following reaction scheme (I):

Scheme I

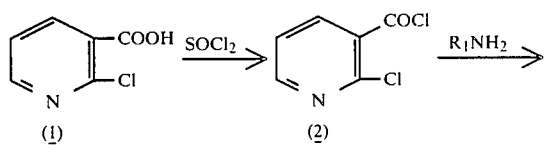

Scheme I
_-continued_

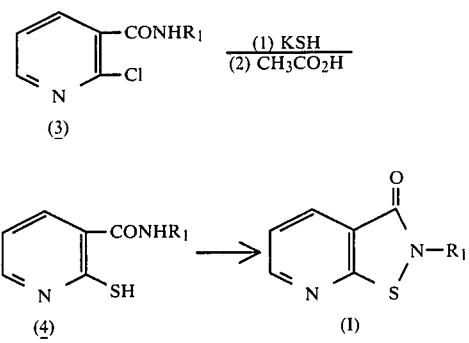

The compounds wherein $R_1$ is a mono- or polyhydroxyalkyl are preferably obtained in accordance with the following reaction scheme:

Scheme II

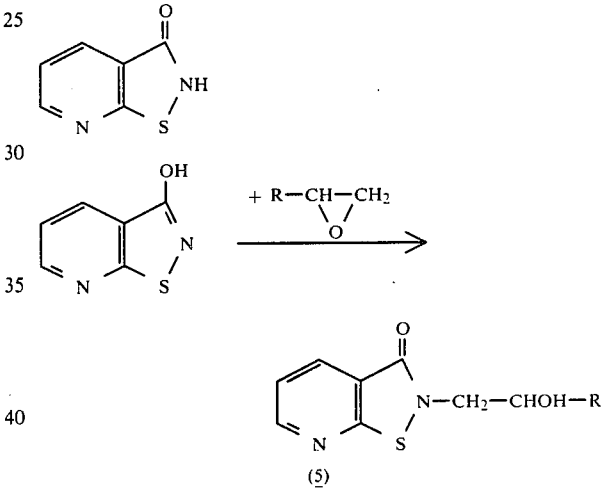

The general method of preparing the active compounds of formula (I) comprises initially preparing 2-chloronicotinamide (3) by reacting an excess of an amine, $R_1NH_2$, with the acid chloride of 2-chloronicotinic acid (2) in solution in 1,2-dichloroethane, optionally in the presence of water.

The 2-mercapto nicotinamides (4) are prepared by the reaction of potassium sulfhydrate on 2-chloronicotinamides (3) solubilized in methyl or ethyl "Cellosolve". After concentrating the reaction medium, the residue is taken up in water and the 2-mercapto nicotinamide (4) is precipitated by adding acetic acid in an amount sufficient so that the pH thereof is about 4, and then purifying the same by crystallization in an appropriate solvent.

The (5,4b) isothiazolo pyridine-3-ones are then obtained by oxidation of the 2-mercapto nicotinamides (4) using sodium metaperiodate fixed on alumina acid, this oxidation reagent being described by Kwang Ting Liu and Yung Chien Tong, J. Org. Chem. 1978, Vol. 43, p. 2717.

With the use of this reagent it is possible to obtain in a selective fashion the (5,4b)-isothiazolo pyridine-3-ones.

The oxidation reaction with metaperiodate is carried out at ambient temperature by adding, all at once, one equivalent of the oxidizing reagent fixed on alumina in an alcoholic solution of 2-mercapto nicotinamide (4).

The reaction is very rapid, i.e. a few minutes. The reaction mixture is then filtered; the alumina is washed with ethanol; and the filtrate is concentrated under reduced pressure thereby providing the expected product which is then purified on a chromatography column of silica gel so as to remove iodine which is liberated during the course of the reaction.

The active compounds of formula (I) wherein $R_1$ represents mono- or polyhydroxyalkyl (5) are prepared starting with (5,4b)-isothiazolo pyridine-3-one, or 3-hydroxy-(5,4b)-isothiazolo pyridine, by reacting it with an epoxide as represented in accordance with Scheme (II).

The following non-limiting examples are given to illustrate the present invention, these examples including methods of preparing the active anti-acne compounds as well as anti-acne compositions.

EXAMPLE I

Preparation of (5,4b) isothiazolo pyridine-3-ones according to reaction Scheme I (1) Preparation of the acid chloride of 2-chloro-1-nicotinic acid (2):

To 17.2 g of 2-chloronicotinic acid (I) (0.11 mole), stirred at ambient temperature and out of contact with the humidity of the air, 70 cc of pure thionyl chloride are added. The resulting reaction mixture is brought to the boiling temperature of thionyl chloride and is maintained at this temperature until a homogeneous medium is established. Generally about 1½ hours are required. The thionyl chloride is then removed by distillation under reduced pressure. The hydrochloride of the acid chloride then crystallizes at ambient temperature in a qualitative yield.

(2) Preparation of 2-chloronicotinamides of the formula

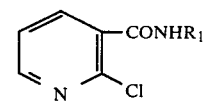
(3)

To a solution of the hydrochloride of the acid chloride obtained according to Example I(1), above, in 1,2-dichloroethane and cooled to 0° C., there is slowly added with stirring an excess of an amine, $R_1NH_2$, either in aqueous solution, or in solution in 1,2-dichloroethane. At the end of the addition, the reaction mixture is permitted to stand for 2 hours at ambient temperature. The resulting organic phase is then decanted, washed with a minimum of ice water and dried on sodium sulfate. After concentration under reduced pressure, the residue is recrystallized in an appropriate solvent. When the amine added is an aqueous solution thereof the decanted aqueous phase is concentrated to dryness and the resulting precipitate is taken up in toluene so as to isolate a portion of the amide slightly soluble in water.

The 2-chloronicotinamides of formula (3) obtained according to this process are set forth in the Table I below:

TABLE I

| Compound n° | $R_1NH_2$ ($R_1$) | Solvent | Yield % | F.°C.* | | C % | H % | Cl % | N % |
|---|---|---|---|---|---|---|---|---|---|
| (3)a | H | 1,2-dichloroethane + water | 95 | 165 (i) | Calc. | 46.02 | 3.22 | 22.64 | 17.89 |
| | | | | | Theory | 46.33 | 3.61 | 22.64 | 17.84 |
| (3)b | —CH₃ | 1,2-dichloroethane + water | 75 | 111 (ii) | Calc. | 49.28 | 4.14 | 20.78 | 16.42 |
| | | | | | Theory | 49.32 | 4.42 | 20.74 | 16.59 |
| (3)c | —C₂H₅ | 1,2-dichloroethane + water | 90 | 40 | Calc. | 52.04 | 4.91 | 19.20 | 15.17 |
| | | | | | Theory | 51.85 | 5.09 | 19.10 | 14.97 |
| (3)d | —CH(CH₃)₂ | 1,2-dichloroethane | 90 | 90 (iii) | Calc. | 54.41 | 5.58 | 17.85 | 14.10 |
| | | | | | Theory | 54.19 | 5.75 | 17.98 | 14.33 |
| (3)e | —nC₈H₁₇ | " | 67 | 38 | Calc. | 62.56 | 7.87 | 13.19 | 10.42 |
| | | | | | Theory | 62.35 | 8.17 | 13.32 | 10.63 |
| (3)f | —C₆H₁₁ | " | 90 | 131 (iv) | Calc. | 60.38 | 6.33 | 14.85 | 11.73 |
| | | | | | Theory | 60.54 | 6.26 | | 12.37 |
| (3)g | —CH₂C₆H₅ | " | 84 | 119 (iv) | Calc. | 63.29 | 4.49 | 14.37 | 11.35 |
| | | | | | Theory | 63.03 | 4.79 | 14.35 | 11.28 |
| (3)h | —C₆H₄—Cl | " | 98 | 150 (iii) | Calc. | 53.95 | 3.02 | 26.55 | 10.49 |
| | | | | | Theory | 53.97 | 3.30 | 26.34 | 10.48 |

TABLE I-continued

| Compound n° | R₁NH₂ (R₁) | Solvent | Yield % | F.°C.* | | Analyses C % | H % | Cl % | N % |
|---|---|---|---|---|---|---|---|---|---|
| (3)i | 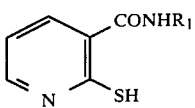 | " | 98 | 205 (v) | Calc. | 47.79 | 2.34 | 35.27 | 9.29 |
| | | | | | Theory | 47.62 | 2.57 | 35.37 | 9.46 |

*Crystallization solvent
(i) benzene-isopropanol
(ii) benzene
(iii) benzene-hexane
(iv) toluene
(v) benzene-chloroform (3) Preparation of 2-mercapto nicotinamides of the formula

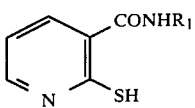

(4)

To a solution of 2-chloro nicotinamide (0.05 mole) such as obtained in Example I(2) above, in methyl or ethyl Cellosolve, there is added at ambient temperature and with stirring, a previously prepared solution of potassium sulfhydrate. This solution is obtained by passing, with stirring and by cooling to 0° C., a stream of hydrogenated sulfide in a solution of 0.11 mole of potassium in 50 cc of methyl Cellosolve until it no longer gives coloration with phenolphthalein.

The mixture thus obtained is heated for 4 hours at 125° C. and then concentrated under reduced pressure. The residue is stirred in 400 cc of water, then acidified by adding sufficient acetic acid until the pH thereof is about 4. The expected 2-mercapto nicotinamide precipitates and then is filtered and dried.

The 2-mercapto nicotinamides of formula (4) obtained according to this process are set forth in the Table II, below.

(4) Preparation of (5,4b)-isothiazolo pyridine-3-ones of the formula

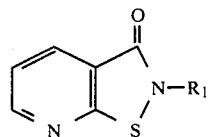

(I)

To a stirred solution of 2-mercapto nicotinamide, obtained in accordance with Example I(3), above, in ethanol or methanol at ambient temperature, there is added, all at once, one equivalent of sodium metaperiodate fixed on alumina. (This reagent is prepared by the method of Kwang Ting Liu and Yung Chien Tong, J. Org. Chem., 1978, 43, p. 2717). The disappearance of the 2-mercapto nicotinamide, which is generally very rapid, is followed by thin layer chromatography. The reaction mixture is filtered; the alumina is washed with methanol; and the filtrate is then concentrated under reduced pressure. The resulting residue is dissolved in a minimum of chloroform and the chloroformic solution is deposited on a chromatography column of silica gel to remove the iodine liberated during the course of the reaction. The (5,4b)-isothiazolo pyridine-3-ones are recrystallized in an appropriate solvent, and then fil-

TABLE II

| Compound n° | R₁ | Yield % | F.°C.* | | Analyses C % | H % | N % | S % |
|---|---|---|---|---|---|---|---|---|
| (4)a | H | 82 | 260 (i) | Calc. | 46.74 | 3.92 | 18.16 | 20.79 |
| | | | | Theory | 46.73 | 4.12 | 18.15 | 20.96 |
| (4)b | —CH₃ | 70 | 217 (ii) | Calc. | 49.98 | 4.79 | 16.65 | 19.06 |
| | | | | Theory | 50.12 | 4.85 | 16.65 | 19.20 |
| (4)c | —C₂H₅ | 75 | 200 (ii) | Calc. | 52.71 | 5.53 | 15.37 | 17.59 |
| | | | | Theory | 52.50 | 5.40 | 15.49 | 17.69 |
| (4)d | —CH(CH₃)₂ | 76 | 178 (iii) | Calc. | 55.08 | 6.16 | 14.27 | 16.34 |
| | | | | Theory | 54.90 | 6.00 | 14.42 | 16.37 |
| (4)e | —nC₈H₁₇ | 93 | 112 (iv) | Calc. | 63.12 | 8.32 | 10.51 | 12.03 |
| | | | | Theory | 63.25 | 8.33 | 10.37 | 12.19 |
| (4)f | —C₆H₁₁ | 92 | 194 (v) | Calc. | 60.99 | 6.92 | 11.85 | 13.57 |
| | | | | Theory | 60.90 | 6.96 | 12.00 | 13.67 |
| (4)g | —CH₂—C₆H₅ | 80 | 176 (i) | Calc. | 63.90 | 4.95 | 11.47 | 13.12 |
| | | | | Theory | 63.80 | 4.92 | 11.54 | 13.02 |

*Crystallization solvent
(i) ethanol
(ii) benzene-ethanol
(iii) benzene-ethanol-hexane
(iv) benzene-hexane
(v) toluene tered and dried. The active compounds of formula (I) obtained according to this process are set forth in Table III, below.

then crystallized in this solvent with a yield of 30%, the product being in the form of white crystals having a melting point of 112° C.

TABLE III

| Compound n° | R$_1$ | Yield % | F.°C.* | | C % | H % | N % | S % |
|---|---|---|---|---|---|---|---|---|
| 1 | —CH$_3$ | 50 | 133 (i) | Calc. | 50.58 | 3.64 | 16.85 | 19.29 |
| | | | | Theory | 50.34 | 3.92 | 16.98 | 19.25 |
| 2 | —C$_2$H$_5$ | 60 | 81 (ii) | Calc. | 53.31 | 4.47 | 15.54 | 17.79 |
| | | | | Theory | 53.26 | 4.38 | 15.64 | 17.76 |
| 3 | —CH(CH$_3$)$_2$ | 81 | 66 (iii) | Calc. | 55.64 | 5.19 | 14.42 | 16.51 |
| | | | | Theory | 55.88 | 5.22 | 14.46 | 16.52 |
| 4 | —nC$_8$H$_{17}$ | 83 | 45 (iii) | Calc. | 63.59 | 7.62 | 10.59 | 12.13 |
| | | | | Theory | 63.66 | 7.64 | 10.59 | 12.28 |
| 7 | —C$_6$H$_{11}$ (cyclohexyl) | 30 | 137 (iii) | Calc. | 61.51 | 6.02 | 11.95 | 13.68 |
| | | | | Theory | 61.45 | 5.98 | 12.19 | 13.45 |
| 8 | —CH$_2$C$_6$H$_5$ | 40 | 75 (iv) | Calc. | 64.44 | 4.16 | 11.56 | 13.23 |
| | | | | Theory | 64.47 | 4.20 | 11.62 | 13.09 |
| 9 | —C$_6$H$_4$—Cl | 72 | 196–198 (v) | Calc. | 54.86 | 2.68 | 10.66 | 12.20 |
| | | | | Theory | 54.71 | 2.96 | 10.85 | 12.46 |
| 10 | —C$_6$H$_3$Cl$_2$ (2,4-dichloro) | 65 | 177–178 (v) | Calc. | 48.50 | 2.03 | 9.43 | 10.79 |
| | | | | Theory | 48.71 | 2.28 | 9.20 | 10.86 |

*Crystallization solvent
(i) benzene/hexane
(ii) methanol
(iii) hexane
(iv) benzene/
(v) acetone

EXAMPLE II

Preparation of (5,4b)-isothiazolo pyridine-3-ones in accordance with Reaction Scheme II (1) Preparation of 3-hydroxy-(5,4b)-isothiazolo pyridine.

To a solution, stirred at ambient temperature, of 3 g of 2-mercapto nicotinamide in 75 cc of acetic acid there are slowly added 7.3 cc of H$_2$O$_2$ at 30 volumes. The reaction medium becomes progressively homogeneous. After a one hour reaction period, 2-mercapto nicotinamide is no longer detected in the reaction medium. The reaction mixture is then concentrated under reduced pressure and the resulting solid is recrystallized in methanol. The 3-hydroxy-(5,4b)-isothiazolo pyridine, obtained in a yield of 2.7 g, is provided in the form of yellow needles having a melting point of 220° C.

Analysis: C$_6$H$_4$N$_2$OS Calculated: C 47.36, H 2.65, N 18.41, S 21.07. Theory: C 47.42, H 2.83, N 18.66, S 21.25.

(2) Preparation of 2-(2-hydroxypropyl)-(5,4b)-isothiazolo pyridine-3-one—Compound No. 5.

There is left to stand at ambient temperature, with stirring and out of contact with the humidity of the air, a mixture of 1 g of 3-hydroxy-(5,4b)-isothiazolo pyridine in 10 cc of propylene oxide in the presence of two drops of 1,5-diaza-[5.4.0]bicyclo-5 undecene (D.B.U.). After 10 days, excess propylene oxide is removed under reduced pressure. The resulting residue is dissolved in chloroform and deposited on a column of silica gel. The expected compound is eluted with ethyl acetate and Analysis: C$_9$H$_{10}$N$_2$O$_2$S Calculated: C 51.41, H 4.79, N 13.32, S 15.25. Theory: C 51.46, H 4.92, N 13.51, S 15.31.

(3) Preparation of 2-(1,2-dihydroxypropyl)-(5,4b)-isothiazolo pyridine-3-one. Compound No. 6.

A mixture of 1 g of 3-hydroxy-(5,4b)-isothiazolo pyridine (6.6 × 10$^{-3}$ mole) in 1 cc of glycidol and 2 drops of D.B.U. is brought to the boiling temperature of tetrahydrofuran for 42 hours. The reaction mixture is then concentrated, taken up in a minimum of chloroform and the resulting solution deposited on a column of silica gel. The expected compound is eluted with acetone, and then recrystallized in this solvent, thus providing a 67% yield of the product in the form of a white powder having a melting point of 125° C.

Analysis: C$_9$H$_{10}$N$_2$O$_3$S Calculated: C 47.78, H 4.46, N 12.28, S 14.17. Theory: C 47.49, H 4.76, N 12.36, S 14.14.

EXAMPLES OF ANTI-ACNE COMPOSITIONS

Example A

An anti-acne milk composition is prepared by admixing the following components:

2-methyl-(5,4b)-isothiazolo pyridine-3-one: 0.5 g
Crosslinked polyacrylic acid, sold under the tradename "Carbopol 934": 0.375 g
Isopropyl ester of the fatty acids of lanolin: 1 g
Oxyethylenated lanolin: 2.5 g
Oxyethylenated cetylstearyl alcohol: 3 g Substituted alkylamide: 20 g
Methyl p-hydroxybenzoate: 0.1 g
Propyl p-hydroxybenzoate: 0.1 g
Water, sufficient amount for: 100 g In this example, the active compound can advantageously be replaced by 2 g of 2-ethyl-(5,4b)-isothiazolo pyridine-3-one.

Example B

An anti-acne milk composition is prepared by the following components:
2-isopropyl-(5,4b)-isothiazolo pyridine-3-one: 1 g
Crosslinked polyacrylic acid sold under the tradename "Carbopol 934": 0.375 g
Isopropyl ester of the fatty acids of lanolin: 1 g
Oxyethylenated lanolin: 2.5 g
Oxyethylenated cetylstearyl alcohol: 3 g
Substituted alkylamide: 20 g
Butylhydroxy toluene: 0.5 g
Water, sufficient amount for: 100 g

Example C

An anti-acne gel composition is prepared by admixing the following components:
2-isopropyl-(5,4b)-isothiazolo pyridine-3-one: 1 g
Carboxyvinyl resin: 1.5 g
Disodium tetracemate: 0.05 g
Propylene glycol: 5 g
Distilled water, amount sufficient for: 100 g In this example, the active compound can advantageously be replaced by 0.5 g of 2-methyl-(5,4b)-isothiazolo pyridine-3-one.

Example D

An anti-acne cream composition is prepared by admixing the following components:
2-methyl-(5,4b)-isothiazolo pyridine-3-one: 1 g
Oxyethylenated cetylstearyl alcohol: 9 g
Stearic acid: 1 g
Isopropyl myristate: 5 g
Diethylene glycol stearate: 10 g
Butylhydroxy toluene: 1 g
Water, sufficient amount for: 100 g In this example the active compound can advantageously be replaced by 3 g of 2-benzyl-(5,4b)-isothiazolo pyridine-3-one.

Example E

An anti-acne lotion composition is prepared by admixing the following components:
2-methyl-(5,4b)-isothiazolo pyridine-3-one: 05. g
Ethanol—95°: 60 g
Water, sufficient amount for: 100 g

Example F

An anti-acne lotion composition is prepared by admixing the following components:
2-isopropyl-(5,4b)-isothiazolo pyridine-3-one: 2 g
Propylene glycol: 30 g
Ethanol, 95°, amount sufficient for: 100 g

Example G

An anti-acne lotion composition is prepared by admixing the following components:
2-methyl-(5,4b)-isothiazolo pyridine-3-one: 1 g
Propylene glycol 400: 10 g
Butyl hydroxytoluene: 0.5 g
Ethanol, sufficient amount for: 100 g

What is claimed is:

1. A process for the treatment of acne comprising applying to the area of the skin affected with acne an effective amount of an anti-acne composition comprising in a carrier suitable for topical application to the skin, 0.05 to 10 percent by weight based on the total weight of said composition of an active compound having the formula

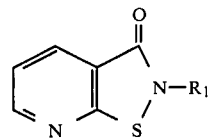

wherein $R_1$ is linear or branched alkyl having 1-12 carbon atoms, mono- or polyhydroxyalkyl having 2-5 carbon atoms, alkenyl having 3-6 carbon atoms, cycloalkyl having 3-6 carbon atoms, or a radical of the formula

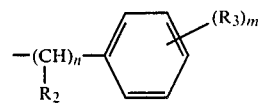

wherein n is 0 or 1, m is 1, 2 or 3, $R_2$ represents hydrogen or lower alkyl having 1-3 carbon atoms and $R_3$ represents hydrogen, alkyl having 1-4 carbon atoms, nitro, $-CF_3$ or halogen, and
the acid salt thereof with a mineral or organic acid.

2. The process of claim 1 wherein the mineral acid is hydrochloric acid or hydrobromic acid.

3. The process of claim 1 wherein $R_1$ represents a mono- or polyhydroxyalkyl having 2-5 carbon atoms, alkenyl having 3-6 carbon atoms or cycloalkyl having 3-6 carbon atoms.

4. The process of claim 1 wherein said active compound is selected from the group consisting of
(1) 2-methyl-(5,4b)-isothiazolo pyridine-3-one,
(2) 2-ethyl-(5,4b)-isothiazolo pyridine-3-one,
(3) 2-isopropyl-(5,4b)-isothiazolo pyridine-3-one,
(4) 2-octyl-(5,4b)-isothiazolo pyridine-3-one,
(5) 2-(2-hydroxypropyl)-(5,4b)-isothiazolo pyridine-3-one,
(6) 2-(1,2-hydroxypropyl)-(5,4b)-isothiazolo pyridine-3-one,
(7) 2-cyclohexyl-(5,4b)-isothiazolo pyridine-3-one,
(8) 2-benzyl-(5,4b)-isothiazolo pyridine-3-one,
(9) 2-(p-chlorophenyl)-(5,4b)-isothiazolo pyridine-3-one, and
(10) 2-(2,5-dichlorophenyl)-(5,4b)-isothiazolo pyridine-3-one.

5. The process of claim 1 wherein said active compound is present in an amount ranging from 0.3 to 3 percent by weight based on the total weight of said composition.

6. The process of claim 1 wherein said carrier is an alcoholic or hydroalcoholic solution.

7. The process of claim 6 wherein the alcohol is ethanol or isopropanol.

8. The process of claim 1 wherein said carrier is in the form of a water-in-oil or oil-in-water emulsion.

9. A process for the treatment of acne comprising applying to the area of the skin affected with acne, 2 to 3 times each day for a period of time ranging from 1 to 6 weeks an effective amount of an anti-acne composition comprising in a carrier suitable for topical application to the skin 0.05 to 10 percent by weight based on the total weight of said composition of an active compound having the formula

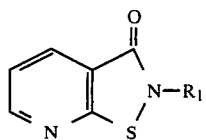

wherein $R_1$ is linear or branched alkyl having 1-12 carbon atoms, mono- or polyhydroxyalkyl having 2-5 carbon atoms, alkenyl having 3-6 carbon atoms, cycloalkyl having 3-6 carbon atoms, or a radical of the formula

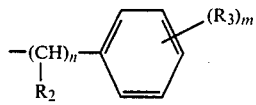

wherein n is 0 or 1, m is 1, 2 or 3, $R_2$ represents hydrogen or lower alkyl having 1-3 carbon atoms and $R_3$ represents hydrogen, alkyl having 1-4 carbon atoms, nitro, $-CF_3$ or halogen, and the acid salt thereof with a mineral or organic acid.

* * * * *